(12) United States Patent
Wang et al.

(10) Patent No.: US 9,856,251 B2
(45) Date of Patent: *Jan. 2, 2018

(54) SUBSTITUTED BERBINES AND PROCESSES FOR THEIR SYNTHESIS

(71) Applicant: Mallinckrodt LLC, Hazelwood, MO (US)

(72) Inventors: Peter X. Wang, Clarkson Valley, MO (US); Frank W. Moser, Arnold, MO (US); Gary L. Cantrell, Troy, IL (US); Christopher W. Grote, Webster Groves, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/235,312

(22) Filed: Aug. 12, 2016

(65) Prior Publication Data

US 2016/0347747 A1 Dec. 1, 2016

Related U.S. Application Data

(63) Continuation of application No. 12/552,457, filed on Sep. 2, 2009, now Pat. No. 9,458,109.

(60) Provisional application No. 61/093,820, filed on Sep. 3, 2008.

(51) Int. Cl.
*C07D 455/03* (2006.01)
*C07D 217/20* (2006.01)
*B01J 31/22* (2006.01)

(52) U.S. Cl.
CPC ........ *C07D 455/03* (2013.01); *B01J 31/2295* (2013.01); *C07D 217/20* (2013.01); *B01J 2231/643* (2013.01); *B01J 2531/821* (2013.01)

(58) Field of Classification Search
None
See application file for complete search history.

(56) References Cited

U.S. PATENT DOCUMENTS

| | | |
|---|---|---|
| 3,101,339 A | 8/1963 | Zeile et al. |
| 4,141,897 A | 2/1979 | Olofson et al. |
| 4,176,186 A | 11/1979 | Goldberg et al. |
| 4,322,426 A | 3/1982 | Hermann et al. |
| 4,368,326 A | 1/1983 | Rice |
| 4,410,700 A | 10/1983 | Rice |
| 4,521,601 A | 6/1985 | Rice |
| 4,535,157 A | 8/1985 | Meltzer et al. |
| 4,556,712 A | 12/1985 | Rice |
| 4,613,668 A | 9/1986 | Rice |
| 4,727,146 A | 2/1988 | Rice |
| 4,794,186 A | 12/1988 | Oine et al. |
| 5,112,975 A | 5/1992 | Wallace |
| 5,240,933 A | 8/1993 | Merz et al. |
| 5,352,680 A | 10/1994 | Portoghese et al. |
| 5,574,159 A | 11/1996 | Chang et al. |
| 5,668,285 A | 9/1997 | Rice et al. |
| 5,869,669 A | 2/1999 | Huang et al. |
| 5,907,069 A | 5/1999 | Becnel et al. |
| 5,922,876 A | 7/1999 | Huang et al. |
| 5,948,788 A | 9/1999 | Huang et al. |
| 5,952,495 A | 9/1999 | Huang et al. |
| 5,981,474 A | 11/1999 | Manning et al. |
| 6,008,354 A | 12/1999 | Huang et al. |
| 6,008,355 A | 12/1999 | Huang et al. |
| 6,013,796 A | 1/2000 | Huang et al. |
| 6,136,817 A | 10/2000 | Schmidhammer |
| 6,174,891 B1 | 1/2001 | Nagase et al. |
| 6,365,742 B1 | 4/2002 | Mudryk et al. |
| 2005/0182258 A1 | 8/2005 | Schmidhammer et al. |
| 2007/0265293 A1 | 11/2007 | Boyd et al. |
| 2008/0064712 A1 | 3/2008 | Schmidhammer et al. |
| 2008/0146804 A1 | 6/2008 | Stumpf |
| 2008/0207906 A1 | 8/2008 | Wang et al. |
| 2009/0270624 A1 | 10/2009 | Weigl et al. |

FOREIGN PATENT DOCUMENTS

| | | |
|---|---|---|
| EP | 0 028 959 | 1/1985 |
| ES | 2 121 554 | 11/1998 |
| PL | 124 001 | 7/1985 |
| WO | WO 01/55117 | 8/2001 |
| WO | WO 2004/029059 | 4/2004 |
| WO | WO 2004/043964 | 5/2004 |
| WO | WO 2006/127899 | 11/2006 |

OTHER PUBLICATIONS

Amaravathi et al., "Oxidation of 1-benzyl-3,4-dihydroisoquinolines using active manganese dioxide," Indian Journal of Chemistry, Section B: Organic Chemistry Including Medicinal Chemisty (1983), 22B(12) 1246-7.

Andreu et al., "An efficient method for the preparation of antitumoral α-keto-imines benzyldihydroisoquinolines by selective benzylic oxidation with C/Pd in acetonitrile," Tetrahedron Letters (2002), 43(5), 757-769.

Archer et al., "1-Acetamido-17-carbomethoxydihydrothebainone," Journal of Heterocyclic Chemistry (1981), 18(2), 357-61.

Baxendale et al., "Enantioselective synthesis of the tetrahydrobenzylisoquinoline alkaloid (−)-norarmepavine using polymer supported reagents," Heterocycles (2003), 60(12), 2707-2715.

Benosman et al., "Synthesis of isoquinolines isolated fro Aniba canelilla", Comptes Rendus de l'Academie des Sciences, Serie II:Mecanique, Physique, Chimie, Sciences de la Terre et de l'Univers, 19983, 316(4), pp. 465-468 (French Language).

Bentley et al., The Reduction of Thebaine and Dihydrothebaine by Sodium and Ammonia, Journal of the Chemical Society, Abstracts (1952), pp. 958-966.

Bermejo et al., "Syntheses and antitumor targeting G1 phase of the cell cycle . . . ", Journal of Medicinal Chemistry, 2002, 45(23), pp. 5058-5068.

(Continued)

*Primary Examiner* — David K O'Dell

(57) ABSTRACT

The present invention provides processes for the synthesis of substituted berbine compounds. Also provided are intermediates used in the synthesis of substituted berbine compounds.

12 Claims, No Drawings

(56) References Cited

OTHER PUBLICATIONS

Beyerman et al., Recl. Trav. Chim. Pays-Bas., 1976, 95, pp. 184.
Bhakuni et al,, "Surthesis of (±)—12-amino derivatives of scoulerine . . . ", Indian Journal of Chemistry, Section B: Organic chemistry Including Medicinal Chemistry, 1985, 248(6), pp. 596-601.
Bhakuni et al., "Studies on mannich reaction of 1-benzyltetrahydroisoquinolines", Journal of the Indian Chemical Society, 1988. 65(6), pp. 417-421.
Bjorklund et al., "Cryptic Stereochemistry of Berberine alkaloid biosynthesis", Journal of the American Chemical Society, 1995, 117(5), pp. 1533-1545.
Boehme et al., "Analogs of M4 selective synthetic muscarinic receptor antagonists: . . . ", Medicinal Chemistry Research, 2002, 11(8), pp. 423-433.
Bognar et al., "Selective Quaternization in the Morphine Series", Tetrahedron Letters, 1964, No. 39, pp. 2867-2871.
Cave et al., "Alkaloids of cryptocarya phyllostemon", Australian Journal of Chemistry, 1989, 42(12), pp. 2243-2263.
Chackalamannil et al., "The synthesis of erythro- and threo-N-methyl-7-hydroxy-1,2,9,10-tetramethoxyaporphine", Tetrahedron Letters, 1980, 21(21), pp. 2029-2032.
Chazerain, "1-Benzoylisoquinolines and their transformation into 1-phenyl-3-benzazepines", Ann. Chim. (Paris), 1963, 8, pp. 255-284.
Cho et al., "Synthesis of 6,7-dimethoxy-1-halobenzyl-1,2,3,4-tetrahydroisoquinolines," Journal of Heterocyclic Chemistry (1999). 36(5), 1151-1156.
Chrzanowska et al., "Asymmetric synthesis of isoquinoline alkaloids," Chemical Reviews (2004), 104, 3341-3370.
Chrzanowska et al., "Synthesis of (S)-(−)- and (R)-(+)-O-methylbharatamine using a diastereoselective Pomeranze-Fritsch-Bobbitt methodology," Tetrahedron: Asymmetry (2005), 16(17), 2954-2958.
Coutts et al., "The enzymatic oxidation of phenolic tetrahydroisoquinoline-1-carboxylic acids," Journal of the Chemical Society, Perkin Transactions 1: Organic and Bio-Organic Chemistry (1972-1999) (1979), (11), 2744-50.
Crooks et al., "Opiate receptor binding properties of morphine-, dihydromorphine-, and codeine 6-0-sulfate ester congeners", Bioorganic & Medicinal Chemistry Letters, 16, 2006, pp. 4291-4295.
Czarnocki, "Enantioselective syntheis of (R)-(−)-calycotomine and (S)-(−)-xylopinine from D-ribonolactone", Journal of Chemical Research, Synopses, 1992, 10, pp. 334-335.
Czarnocki et al., "Asymmetric synthesis of isoquinoline alkaloids. (R)- and (S)-2-(ethoxycarbonyl)-1-formyl-6, . . . ", bulletin des Societes Chimiques Belges, 1986, 95(9-10), pp. 749-770.
Davis et al., "Asymmetric Synthesis of the Porotoberberine Alkaloid (S)-(−)-xylopinine Using Enatiopure Sulfinimines", Journal of Organic Chemistry, 2002, 67(4), pp. 1290-1296.
Degraw et al., J. Het. Chem., Jun. 1974, pp. 363.
Fry et al., Mannich Derivatives of Analgesic Agents, Journal of Organic Chemistry (1959), 24, pp. 116-117.
Funke et al., A¹H and ¹³C Nuclear Magnetic Resonance Study of Three Quaternary Salts of Naloxone and Oxymorphone, J. Chem. Soc. Perkin Trans. (1986) 2. pp. 735-738.
Giger et al., Synthesis and Reactions of the diels-Alder Adduct of Thebaine with 4-phenyl-1,2,4-triazoline-3,5-dione, Tetrahedron (1973), 29(16), pp. 2387-2391.
Gupta et al., "Synthetic photochemistry: Synthesis of liriodenine," Indian Journal of Chemistry, Section B: Organic Chemistry Including Medicinal Chemistry (1983), 22B(5), 429-31.
Hanaoka et al., "Chemical transformation of protoberberines. VIII. A novel synthesis of (±)-fumaricine and a formal synthesis of (±)-alpinigenine," Chemical and Pharmaceutical Bulletin (1985), 33(6), 2273-80.
Hirai et al., "A new preparation of an ochotensin-type isoquinoline by photolysis," Heterocycles (1984), 22(6), 1359-62.

Hu et al., "Photosynthesis of tetrahydroprotoberberines with electron-withdrawing groups on ring D," Chinese Chemical Letters (1998), 9(8), 707-710.
Iorio et al., "Diastereoisomeric Quaternary Morphinium Salts: Synthesis, Stereochemistry and Analgesic Properties", European Journal of Medicinal Chemistry, 1984, 19(1), pp. 11-16.
Kaldor et al., "Stereocontrolled synthesis of cis-dibenzoquinolizine chlorofumarates: curare-like agents of ultrashort duration," Journal of Organic Chemistry (2001), 66(10), 3495-3501.
Kametani et al., "Studies on the syntheses of heterocyclic compounds. DCXCII. A novel synthetic route to phthalideisoquinoline and spirobenzylisoquinoline type alkaloids," Chemical and Pharmaceutical Bulletin (1977), 25(2), 321-6.
Kametani et al., "Studies on the syntheses of heterocycloc compounds. DCXCII. A stereoselective Total Synthesis of (±)-Ophiocarpine; a Simple Route to 13-Hydroxyberbines", JCS Perkin I, 1977, pp. 376-382.
Kametani et al., "Studies on the syntheses of heterocyclic compounds. DCXCIII. A total synthesis of atheroline by photolysis," Tertrahedron (1977), 33(9), 1069-71.
Kametani et al., "Synthesis of oxoaporphine by photolysis. Total synthesis of atheroline," Heterocycles (1975), 3(10), 821-5.
Kapadia et al., "Facile oxidative formation of O-methylvelucryptine during synthesis of dl-O-methylarmepavine," Indian Journal of Pharmaceutical Sciences (1992), 54(6), 227-33.
Kessar et al., "Synthetic Photochemistry: Synthesis of (±)-oliveridine," Indian Journal of Chemistry, Section B: Organic Chemistry Including Medicinal Chemistry (1983), 22B(4), 321-4.
Koczka et al., Selective Quaternization of Compounds with Morphine Skeleton, Acta. Chim. Acad. Sci. Hung. (1967), 51(4), pp. 393-402.
Kunitomo et al., "Synthesis of a few trimethoxyoxoaporphines," Yakugaku Zasshi (1979), 99(1), 102-5. (Japanese language).
Kuo et al., "Antiplatelet activity of benzylisoquinoline derivatives oxidized by cerium (IV) ammonium nitrate," Bioorganic and Medicinal Chemistry Letters (2003), 13(16), 2789-2793.
Lebœuf et al., "Velucryptine, A new isoquinoline alkaloid from cryptocarya velutinosa," Journal of Natural Products (1989), 52(3), 516-21.
Lenz et al., "Lead tetraacetate mediated oxidation of the enamides derived from 1-benzyl-3,4-dihydroisoquinolines," Journal of Organic Chemistry (1988), 53(6), 1176-83.
Lenz et al., "Synthesis of the novel isoquinoline enamide alkaloid polycarpine," Journal of Heterocyclic Chemistry (1981), 18(4), 691-3.
Lopez et al., Photoxidation of Thebaine. A Route to 14-Hydroxymorphinones and Hydrodibenzofuran Analogs of Methadone, Tetrahedron Letters (1994), 35(31), pp. 5727-5730.
Lopez et al., The [4+2] Addition of Singlet Oxygen to Thebaine: New Access to Highly Functionalized Morphine Derivatives via Opioid Endoperoxides, J. Org. Chem. (2000), 65(15), pp. 4671-4678.
Manoharan et al., "Convenient Method for Replacement of Tertiary N-Methyl by Other Alkyl Groups: Application to Morphine Alkaloids", Indian Journal of Chemistry, 1984, vol. 19, No. 1, pp. 5-11.
Manoharan et al., Stereoselectivity in Quaternization of Thebaine: 270 MHz PMR Spectroscopic Studies, Indian Journal of Chemistry, Section B: Organic Chemistry Including Medicinal chemistry (1987), 26B(2), pp. 140-142.
Markaryan et al., "Isoquinoline derivatives. XI. Synthesis and pharmacological activity of 1-arylalkyl-4-spirocyclohexane-6,7-dimethoxy-1,2,3,4-tetrahydroisoquinolines and some of their derivatives," Armyanskii Khimicheskii Zhurnal (1975), 28(10), 829-35. (Russian language).
Martin el al., "Oxidation of imines by selenium dioxide," Zeitschrift fuer Naturforschung, Teil B: Anorganische Chemie, Organische Chemie (1986), 41B(10), 1260-4.
Martin et al., "Regiospecific oxidation of substituted 1-benzyl-3,4-dihydroisoquinolines using singlet oxygen," Tetrahedron Letters (1980), 21(27), 2613-16.
Martin et al., "Synthesis and photooxygenation of some substituted 1-benzyl-3,4-dihydroisoquinolines, Mechanism of enamine photooxygenation," Helvetica Chimica Acta (1982), 65(3), 762-74.

(56) References Cited

OTHER PUBLICATIONS

McMahon et al., "Rearrangement of 1-(α-hydroxybenzyl)-1,2,3,4-tetrahydroisoquinolines to 1-phenyl-2,3,4,5-tetrahydro-1H-3-benzazepines," Journal of the Chemical Society, Perkin Transactions 1: Organic and Bio-Organic Chemistry (1972-1999) (1982). (9), 2163-7.

Memetzidis et al., "Synthesis of aromatic chloroberbines," Heterocycles (1990), 31(2), 341-51.

Meuzelaar et al., "Chemistry of opium alkaloids, Part 45. Improvements in the total synthesis of morphine," European Journal of Organic Chemistry (1999), 2315-2321.

Meyers et al., "Asymmetric synthesis of isoquinoline alkaloids", Tetrahedron, 1987, 43(21), pp. 5095-5108.

Meyers et al., "High enantioselective alkyation of tetrahydroisoquinolines with a chiral valinol derivative . . . ", Angewandte Chemie, 1984, 16(6), pp. 448-449.

Miller et al., "Synthesis and biological evaluation of fragmented derivatives of tetrahydroisoquinolines. 2. Trimetoquinol studies", Journal of Medicinal Chemistry, 1975, 18(5), pp. 454-457.

Mujahidin et al., "Enantioselective synthesis of (+)-(S)-laudanosine and (−)-(S)-xylopinine," European Journal of Organic Chemistry (2005), 2689-2693.

Musich et al., Reaction of O-methyl-N, $N^1$-Diisopropylisourea with Amino Acids and Amines, Journal of Organic Chemistry (1977), 42(1), pp. 139-141.

Nagata et al., Synthetic Studies on Isoquinoline Alkaloids. I. An Efficient Synthesis of 9,10-Substituted Protoberberine Alkaloids 1, Chem. Pharm. Bull. 23(11) 1975, pp. 2867-2877.

Naito et al., "Asymmetric synthesis of dibenzo[a,g]quinolizines related to protoberberine alkaloids,". Heterocycles. (1983), 20(5). 779-82.

Naito et al., "Reductive photocyclization of enamides and its application to alkaloid synthesis", Kobe Women's Coll. Pharm., Tennen Yuki Kagobutsu Toronkai Koen Yoshishu, $24^{th}$, 1981, pp. 460-465.

Naito et al., "Reductive photocyclization of enamide in the presence of a chrial metal hydride complex . . . ", Kobe Women's Coll. Pharm., Heterocycles, 1981, 16(7), pp. 1141-1143.

Ninan et al., "An Improved Synthesis of Noroxymorphone", Tetrahedron, 48(32), 1992, pp. 6709-6716.

Orito et al., "Aryl radical cyclizations of 1-(2'-Bromobenzyl)isoquinolines with AIBN-Bu3SnH: Formation of aporphines and Indolo[2,1-a]isoquinolines," Organic Letters (2000), 2(3), 307-310.

Orito et al., "New synthesis of phthalideisoquinoline alkaloids via a stereoselective hydride reduction of 1-(2'-bromobenzoyl)-3,4-dihydroisoquinoline methiodide, followed by palladium-catalyzed carbonylation aided by chlorotrimethylsilane," Synlett (1994), (4), 245-6.

Orito et al., "Synthesis of (±)-norcoralydine and (±)-tetrahydropalmatine," Organic Preparations and Procedures International (1989), 21(3), 309-14.

Orito et al., "Synthesis of phthalideisoquinoline and protoberberine alkaloids and indolo [2,1-a] isoquinolines in a divergent route involving palladium(0)-catalyzed carbonylation," Journal of Organic Chemistry (1999), 64(18), 6583-6596.

Otto et al., Selection and Amplification of Hosts from Dynamic combinatorial Libraries of Macrocyclic Disulfides, Science (Washington, DC, United States) (2002), 297(5581), pp. 590-593 & Supporting Online Material.

Rice, "Synthetic Opium Alkaloids and Derivatives. A Short total Synthesis . . . ", J. Org. Chem., 1980, 45, pp. 3135-3137.

Rozwadowska et al., "Mammalian alkaloids: O-methylation of (S)- and (R)-dideoxynorlaudanosoline-1-carboxylic acid by catechol O-methyltransferase and identification of a yellow pigment obtained at physiological pH," Helvetica Chimica Acta (1988), 71(7), 1598-607.

Schultz et al., Thebaine Cyclopropanation, Russian Journal of Organic chemistry (Translation of Zhurnal Organicheskoi Khimii) (2003), 39(8), pp. 1083-1088.

Seki, Isao, Studies on the Morphine Alkaloids and its Related Compounds. XIV. Preparation of 6-Amino-hydrophenanthrene Compounds from Hofmann Degradation Products of the Morphine Alkaloids, Chemical & Pharmaceutical Bulletin (1966), 14(5), pp. 453-461.

Shklyaev et al., "A new approach to synthesis of 3,3-dialkyl-3,4-dihydroisoquinoline derivatives," Heteroatom Chemistry (2004), 15(7), 486-493.

Shults et al., Tranformations of Quaternary Tetrahydrothebaine Sulfones, Zh. Org. Khim. (1993), 29(6), pp. 1149-1162, (English pp. 953-963).

Simanek et al., "Synthesis of hypecorine and hypecorinine analogs from 3,4-dihydropapaverine," Symp. Pap. IUPAC Int. Symp. Chem. Nat. Prod., 11th (1978), vol. 2, 58-60.

Simanek et al., "Isolation and chemistry of alkaloids from some plants of the family Papaveraceae. Part LXXIV. Synthesis of hypecorine and hypecorinine analogs from 3,4-dihydropapaveriine", Heterocycles, 1978, 9(9), pp. 1233-1240.

Sladkov et al., "2,3,10,11-Tetramethoxy-5,6,7,8,13,13a-hexahydroprotoberberines and their B-seco analogs: Synthesis and antineoplastic activity," Khimiko-Farmatsevticheskii Zhurnal (1989), 23(1), 50-3. (Russian language).

Sladkov et al., "Benzophenanthridines. VI. Conversions of protoberberine alkaloids into benzo[c]phenanthridines. Hofmann degradation of α-N- and β-N-methyl-(±)-13α-hydroxyxylopinine iodides," Zhurnal Organicheskoi Khimii (1989), 25(4), 854-62 (Russian language).

Tolkachev et al., "Application of the Willgerodt-Kindler reaction in the synthesis of the 1-benzyl-1,2,3,4-tetrahydroisoquinoline alkaloids and their derivatives," Symp. Pap. IUPAC Int. Symp. Chem. Nat. Prod., 11th (1978), vol. 3, 47-50.

Trifonov et al., "Application of organic photochemistry in the synthesis of (±)-glaucine," Izvestiya po Khimiya (1978), 11(2), 297-304.

Trifonov et al., "Berbin-8-ones from 2'-halo-1-benzylisoquinolines and metal carbonyls," Tetrahedron Letters (1985), 26(26), 3159-62.

Uematsu et al., "Asymmetric transfer hydrogenation of imines," Journal of the American Chemical Society (1996), 118, 4916-4917.

Walterova et al., "Isolation and chemistry of the alkaloids from some plants of the genus *Papaver*. LXXVII. Pseudobase formation in 2-methylpapaverinium cations and their biotransformation by enzymes of rat liver homogenates in vitro," Collection of Czechoslovak Chemical Communications (1980), 45(3), 956-65.

Wert et al., "Hofmann degradation of β-hydroxy ammonium salts, α- and β-hydroxylaudanosine, 7-hydroxyglaucine, and 13-hydroxyxylopinine," Journal of Organic Chemistry (1982), 47(26), 5141-50.

Williams et al., "One-pot formation of nitrogen-containing heterocyclic ring systems using a deprotection-cyclization-asymmetric reduction sequence," Chemical Communications Cambridge, United Kingdom) (2005), (37), 4735-4737.

Yamada et al., "Studies on 1,2,3,4-tetrahydroisoquinolines. VI. Reutilization of the unwanted (R)-isomer of (S)-(−)-5,7-dihydroxy-1-(3,4,5-trimethoxybenzyl)-1,2,3,4-tetrahydroisoquinoline (TA-073)," Chemical and Pharmaceutical Bulletin (1983), 31(1), 70-4.

Zhao et al., "Synthesis of nitrones from 3,4-dihydroquinoline derivatives by oxidation with m-chloroperoxybenzoic acid," Organic Preparations and Procedures International (1997), 29(2), 185-194.

Grewe et al., "Die Syntese der Homiosovanillinsaure und ihre . . . ", Chemische Berichte, 96, 1963, pp. 1520-1528, XP 002560192.

Buchs et al., "69. Aromatization of 1-Benzyletrahydroisoquinolines: Racemization of (−)-(S)-(N-nor)-Reticuline", Helvetica Chimica Acta, 64, 1981, pp. 681-686, XP 002560193.

Spath et al., "Uber Alkaloide der colombowurzel . . . ", Chemische Berichte, 75, 1942, pp. 400-407, XP 002560194.

Saha et al., "Synthesis and In Vitro Platelet Aggregation ad TP . . . ", Bioorganic and Medicinal Chemistry, 10, 2002, pp. 2779-2793, XP 002560195.

Chen et al., "Thalifaurine and Dehydrodiscretine, new Quaternary Protoberberines from thalictrum Fauriei", Journal of Pharmaceutical Sciences, 69(9), 1980, pp. 1061-1065, XP 002560196.

(56) References Cited

OTHER PUBLICATIONS

Kametani et al., "A Modified Sunthesis of Codamine Under Eschweiler Clarke Conditions I Corydalis-Pseudoadunca-D Alkaloid", Journal of Heterocyclic Chemistry, 5(6), 1968, pp. 753-755, XP 009126936.

Kametani et al., "Studies on the syntheses of heterocyclic compounds", Journal of the Chemical Society, 1969, pp. 2036-2038, XP 009126947.

SUBSTITUTED BERBINES AND PROCESSES FOR THEIR SYNTHESIS

CROSS-REFERENCE TO RELATED APPLICATIONS

This application is a continuation application of U.S. patent application Ser. No. 12/552,457, now U.S. Pat. No. 9,458,109, filed Sep. 2, 2009, which claims priority to U.S. Provisional Application Ser. No. 61/093,820, filed Sep. 3, 2008, the disclosure of each is hereby incorporated by reference in its entirety.

FIELD OF THE INVENTION

The present invention generally relates to processes for the synthesis of substituted berbines and intermediate compounds used in the preparation of substituted berbines.

BACKGROUND OF THE INVENTION

The berbine class of heterocyclic compounds is structurally related to the plant alkaloid berberine. Berbine compounds have been reported to have numerous therapeutic effects. For example, they supposedly have antibacterial, antifungal, antiparasitic, antipyretic, antihypertensive, antidepressant, antiemetic, tranquilizing, and analgesic activities. Because of the potential therapeutic value of berbine compounds and derivatives thereof, there is a need for efficient synthesis processes for the preparation of pure preparations of specific enantiomers.

SUMMARY OF THE INVENTION

The present invention provides processes for the synthesis of substituted berbine compounds. Also provided are intermediate compounds used in the preparation of substituted berbine compounds.

Among the various aspects of the present invention is one aspect encompassing a process for preparing compound 9 from compound 7. The process comprises contacting compound 7 with an aldehyde in the presence of a proton donor or a proton acceptor to form compound 9 according to the following reaction scheme:

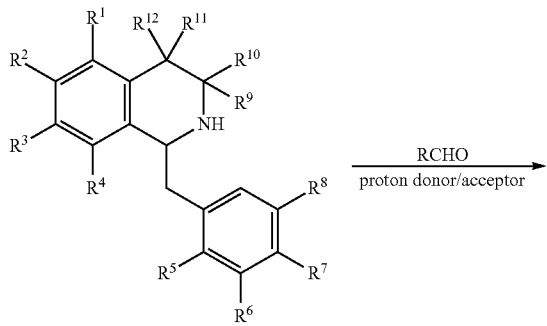

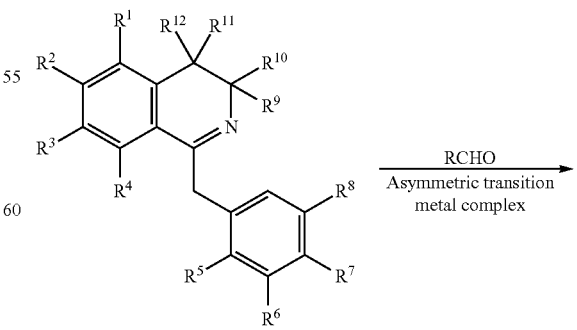

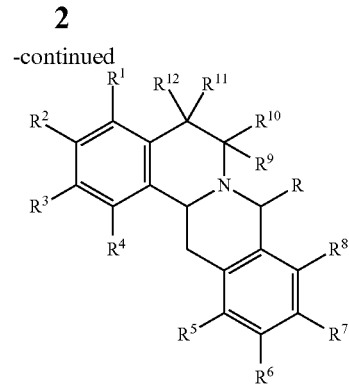

9 wherein:

R is selected from the group consisting of hydrogen, hydrocarbyl, and substituted hydrocarbyl;

$R^1$, $R^4$, $R^5$, and $R^8$ are independently selected from the group consisting of hydrogen, halogen, $OR^{13}$, $NO_2$, hydrocarbyl, and substituted hydrocarbyl;

$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising {—}O(CH$_2$)$_n$O{—}, and $R^6$ and $R^7$ together with the aromatic carbons to which they are attached may form a ring comprising {—}O(CH$_2$)$_n$O{—};

$R^9$, $R^{10}$, $R^{11}$, and $R^{12}$ are independently selected from the group consisting of hydrogen, hydrocarbyl, and substituted hydrocarbyl;

$R^{13}$ is selected from the group consisting of hydrogen, hydrocarbyl, and substituted hydrocarbyl; preferably an alkyl group with 1 to 8 carbon atoms; and n is an integer from 1 to 3.

Another aspect of the invention provides a process for preparing compound 9 from compound 6. The process comprises contacting compound 6 with an aldehyde in the presence of a asymmetric transition metal catalyst to form compound 9 according to the following reaction scheme:

-continued

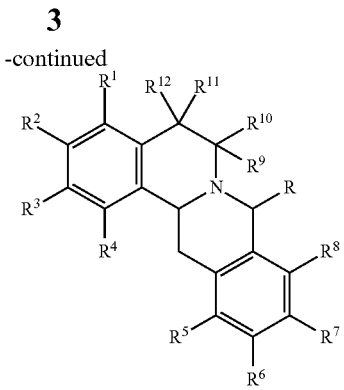

9 wherein:

R is selected from the group consisting of hydrogen, hydrocarbyl, and substituted hydrocarbyl;

$R^1$, $R^4$, $R^5$, and $R^8$ are independently selected from the group consisting of hydrogen, halogen, $OR^{13}$, $NO_2$, hydrocarbyl, and substituted hydrocarbyl;

$R^2$, $R^3$, $R^6$, and $R^7$ are independently selected from the group consisting of hydrogen, $OR^{13}$, hydrocarbyl, and substituted hydrocarbyl, provided that $R^2$ and $R^3$ together with the aromatic carbons to which they are attached may form a ring comprising {—}O(CH$_2$)$_n$O{—}, and $R^6$ and $R^7$ together with the aromatic carbons to which they are attached may form a ring comprising {—}O(CH$_2$)$_n$O{—};

$R^9$, $R^{10}$, $R^{11}$, and $R^{12}$ are independently selected from the group consisting of hydrogen, hydrocarbyl, and substituted hydrocarbyl;

$R^{13}$ is selected from the group consisting of hydrogen, hydrocarbyl, and substituted hydrocarbyl, preferably an alkyl group with 1 to 8 carbon atoms; and n is an integer from 1 to 3.

A further aspect of the invention encompasses a two-step method for the preparation of compound 9 from compound 6 according to the following reaction scheme:

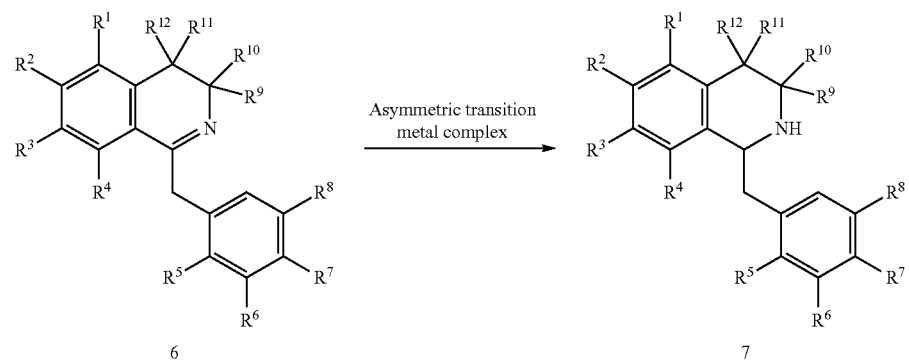

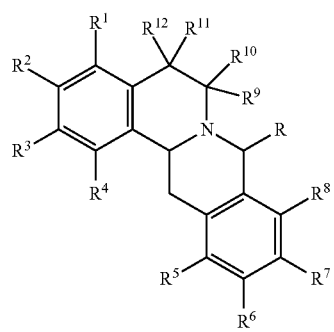

9 wherein:

R is selected from the group consisting of hydrogen, hydrocarbyl, and substituted hydrocarbyl;

$R^1$, $R^4$, $R^5$, and $R^8$ are independently selected from the group consisting of hydrogen, halogen, $OR^{13}$, $NO_2$, hydrocarbyl, and substituted hydrocarbyl;

$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising $\{-\}O(CH_2)_nO\{-\}$, and $R^6$ and $R^7$ together with the aromatic carbons to which they are attached may form a ring comprising $\{-\}O(CH_2)_nO\{-\}$;

$R^9$, $R^{10}$, $R^{11}$, and $R^{12}$ are independently selected from the group consisting of hydrogen, hydrocarbyl, and substituted hydrocarbyl;

$R^{13}$ is selected from the group consisting of hydrogen, hydrocarbyl, and substituted hydrocarbyl, preferably an alkyl group with 1 to 8 carbon atoms; and n is an integer from 1 to 3.

Still another aspect provides a process for the preparation of compound 9x according to the following reaction scheme:

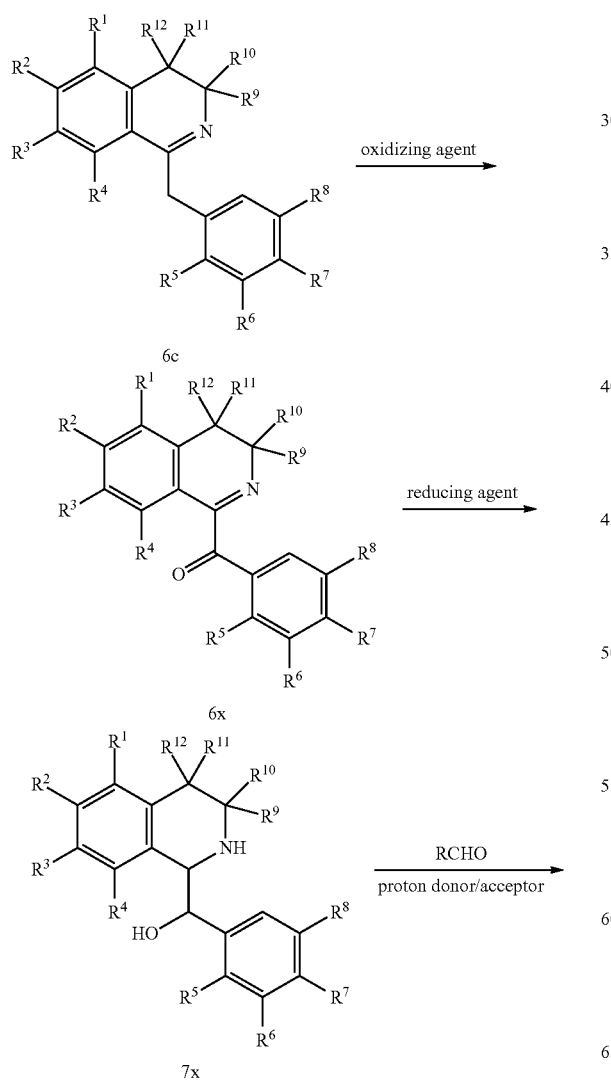

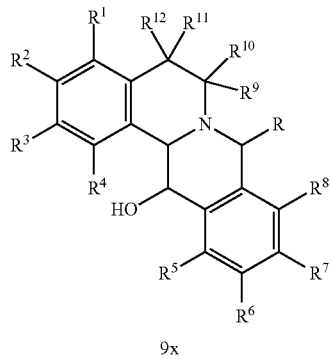

9x wherein:

R is selected from the group consisting of hydrogen, hydrocarbyl, and substituted hydrocarbyl;

$R^1$, $R^4$, $R^5$, and $R^8$ are independently selected from the group consisting of hydrogen, halogen, $OR^{13}$, $NO_2$, hydrocarbyl, and substituted hydrocarbyl;

$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising $\{-\}O(CH_2)_nO\{-\}$, and $R^6$ and $R^7$ together with the aromatic carbons to which they are attached may form a ring comprising $\{-\}O(CH_2)_nO\{-\}$;

$R^9$, $R^{10}$, $R^{11}$, and $R^{12}$ are independently selected from the group consisting of hydrogen, hydrocarbyl, and substituted hydrocarbyl;

$R^{13}$ is selected from the group consisting of hydrogen, hydrocarbyl, and substituted hydrocarbyl, preferably an alkyl group with 1 to 8 carbon atoms; and n is an integer from 1 to 3.

Yet another aspect of the invention encompasses a process for preparing compound 10. The process comprises contacting compound 8 with formaldehyde to form compound 10 according to the following reaction scheme:

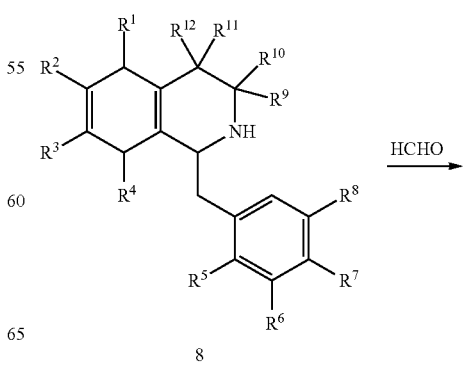

-continued

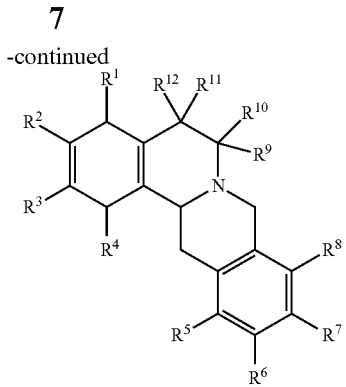

wherein:
$R^1$, $R^4$, $R^5$, and $R^8$ are independently selected from the group consisting of hydrogen, halogen, $OR^{13}$, $NO_2$, hydrocarbyl, and substituted hydrocarbyl;
$R^2$, $R^3$, $R^6$, and $R^7$ are independently selected from the group consisting of hydrogen, halogen $OR^{13}$, hydrocarbyl, and substituted hydrocarbyl, provided that $R^2$ and $R^3$ together with the aromatic carbons to which they are attached may form a ring comprising $\{-\}O(CH_2)_nO\{-\}$, and $R^6$ and $R^7$ together with the aromatic carbons to which they are attached may form a ring comprising $\{-\}O(CH_2)_nO\{-\}$;
$R^9$, $R^{10}$, $R^{11}$, and $R^{12}$ are independently selected from the group consisting of hydrogen, hydrocarbyl, and substituted hydrocarbyl;
$R^{13}$ is selected from the group consisting of hydrogen, hydrocarbyl, and substituted hydrocarbyl, preferably an alkyl group with 1 to 8 carbon atoms; and
n is an integer from 1 to 3.

A further aspect of the invention provides a compound comprising Formula (I):

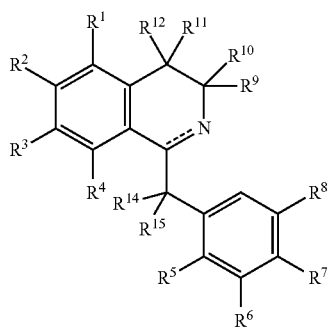

wherein:
$R^1$, $R^4$, $R^5$, and $R^8$ are independently selected from the group consisting of hydrogen, halogen, $OR^{13}$, $NO_2$, hydrocarbyl, and substituted hydrocarbyl;
$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising $\{-\}O(CH_2)_nO\{-\}$, and $R^6$ and $R^7$ together with the aromatic carbons to which they are attached may form a ring comprising $\{-\}O(CH_2)_nO\{-\}$;
$R^9$, $R^{10}$, $R^{11}$, and $R^{12}$ are independently selected from the group consisting of hydrogen, hydrocarbyl, and substituted hydrocarbyl;
$R^{13}$ is selected from the group consisting of hydrogen, hydrocarbyl, and substituted hydrocarbyl, preferably an alkyl group with 1 to 8 carbon atoms;
$R^{14}$ and $R^{15}$ are independently selected from the group consisting of hydrogen, hydroxy, and alkoxy, wherein $R^{14}$ and $R^{15}$ together may form =O;
n is an integer from 1 to 3; and
— is a single or double bond.

Other aspects and features of the invention will be in part apparent and in part pointed out hereinafter.

DETAILED DESCRIPTION

The present invention provides processes for preparing substituted berbines, as well as intermediate compounds for use in the preparation of substituted berbines. These processes of the invention are more efficient, more specific, and provide greater yields than currently available synthesis processes. Additionally, the substituted berbines may be more specific, more efficacious, more potent, and/or have fewer untoward effects than unsubstituted berbines.

For ease of discussion of the substituted berbine compounds and their intermediates, the ring atoms of a berbine compound are numbered as

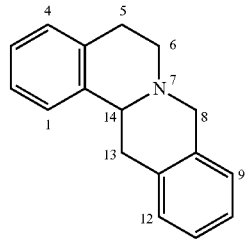 [SMILES: c1ccc2c(c1)CC1c3ccccc3CCN1C2]

diagrammed below. The substituted berbine compounds detailed herein may have as many as three chiral carbons, namely, C-14, C-13, and C-8.

(I) Intermediate Compounds

One aspect of the present invention encompasses compounds that may be used as intermediates in the preparation of a substituted berbine compound. In general, the intermediate compounds comprise Formula (I):

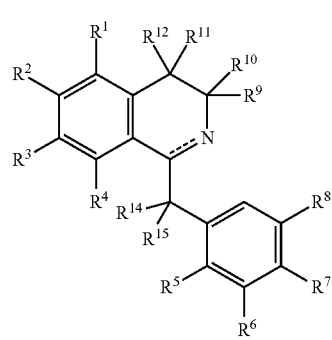

wherein:
$R^1$, $R^4$, $R^5$, and $R^8$ are independently selected from the group consisting of hydrogen, halogen, $OR^{13}$, $NO_2$, hydrocarbyl, and substituted hydrocarbyl;

R², R³, R⁶, and R⁷ are independently selected from the group consisting of hydrogen, halogen, OR¹³, hydrocarbyl, and substituted hydrocarbyl, provided that R² and R³ together with the aromatic carbons to which they are attached may form a ring comprising {—}O(CH₂)ₙO{—}, and R⁶ and R⁷ together with the aromatic carbons to which they are attached may form a ring comprising {—}O(CH₂)ₙO{—};

R⁹, R¹⁰, R¹¹, and R¹² are independently selected from the group consisting of hydrogen, hydrocarbyl, and substituted hydrocarbyl;

R¹³ is selected from the group consisting of hydrogen, hydrocarbyl, and substituted hydrocarbyl, preferably an alkyl group with 1 to 8 carbon atoms;

R¹⁴ and R¹⁵ are independently selected from the group consisting of hydrogen, hydroxy, and alkoxy, wherein R¹⁴ and R¹⁵ together may form =O;

n is an integer from 1 to 3; and

— is a single or double bond.

In one embodiment, the compound comprises Formula (Ia):

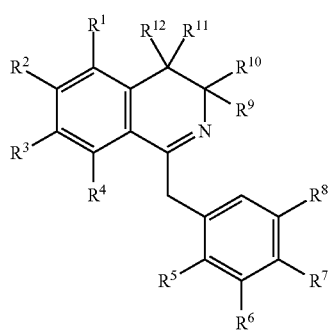

(Ia)

wherein R¹, R², R³, R⁴, R⁵, R⁶, R⁷, R⁸, R⁹, R¹⁰, R¹¹, and R¹² are as defined above.

In one iteration of this embodiment, R⁹, R¹⁰, R¹¹, and R¹² are each hydrogen.

In another embodiment, the compound comprises Formula (Ib):

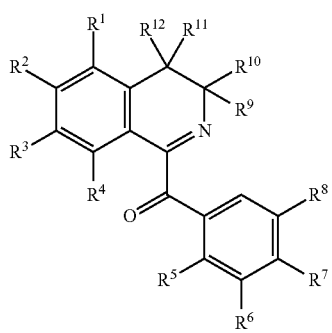

(Ib)

wherein R¹, R², R³, R⁴, R⁵, R⁶, R⁷, R⁸, R⁹, R¹⁰, R¹¹, and R¹² are as defined above.

In an iteration of this embodiment, R⁹, R¹⁰, R¹¹, and R¹² are each hydrogen.

In a further embodiment, the compound comprises Formula (Ic):

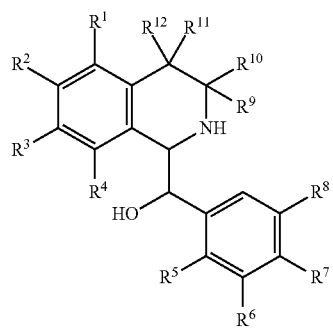

(Ic)

wherein R¹, R², R³, R⁴, R⁵, R⁶, R⁷, R⁸, R⁹, R¹⁰, R¹¹, and R¹² are as defined above.

In one iteration of this embodiment, R⁹, R¹⁰, R¹¹, and R¹² are each hydrogen. The optical activity of this compound may be either (+) or (−), and the configuration of the chiral carbons, C-14 and C-13, may be RR, RS, SR or SS, respectively.

(II) Processes for Preparing Substituted Berbine Compounds

Another aspect of the present invention provides reaction schemes for the preparation of substituted berbine compounds. In general, the processes entail formation of a new ring from an asymmetric compound.

(a) Reaction Scheme 1: Conversion of Compound 7 to Compound 9

Reaction Scheme 1 provides a process in which the asymmetric compound, compound 7, undergoes a ring closure in the presence of an aldehyde and a proton donor or a proton acceptor to form the substituted berbine, compound 9, as depicted below:

Reaction Scheme 1

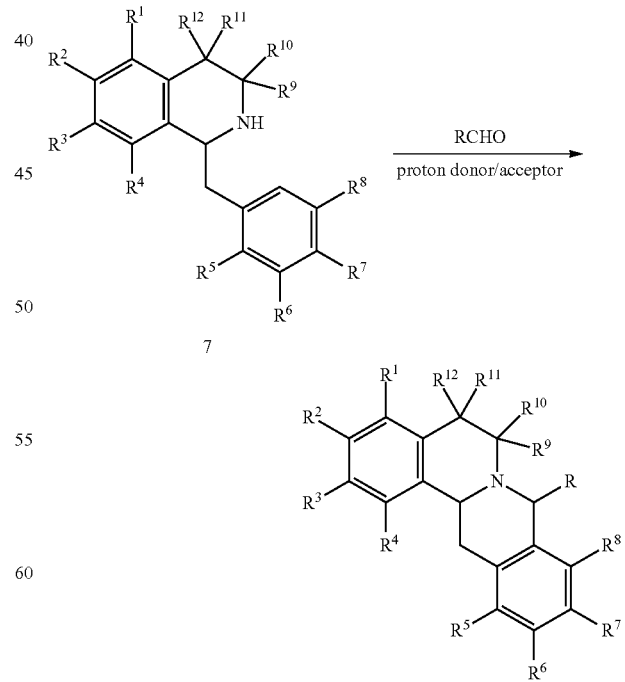

wherein:
R is selected from the groups consisting of hydrogen, hydrocarbyl, and substituted hydrocarbyl;
$R^1$, $R^4$, $R^5$, and $R^8$ are independently selected from the group consisting of hydrogen, halogen, $OR^{13}$, $NO_2$, hydrocarbyl, and substituted hydrocarbyl;
$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising {—}O(CH$_2$)$_n$O{—}, and $R^6$ and $R^7$ together with the aromatic carbons to which they are attached may form a ring comprising {—}O(CH$_2$)$_n$O{—};
$R^9$, $R^{10}$, $R^{11}$, and $R^{12}$ are independently selected from the group consisting of hydrogen, hydrocarbyl, and substituted hydrocarbyl;
$R^{13}$ is selected from the group consisting of hydrogen, hydrocarbyl, and substituted hydrocarbyl, preferably an alkyl group with 1 to 8 carbon atoms; and
n is an integer from 1 to 3.

In an alternative of this embodiment, R is selected from the group consisting of hydrogen, alkyl, aryl, carboxylic acid, and a heterocyclic ring; and $R^9$, $R^{10}$, $R^{11}$, and $R^{12}$ are each hydrogen. In a preferred alternative of this embodiment, R is hydrogen.

The process of Reaction Scheme 1 comprises contacting compound 7 with an aldehyde (i.e., RCHO) in the presence of a proton donor or a proton acceptor to form compound 9. Non-limiting examples of suitable aldehydes include formaldehyde, acetaldyhyde, propionaldehyde, butyraldehyde, cyclopropane carboxaldehyde, cyclobutane carboxaldehyde, benzaldehyde, glyoxal, glyoxylic acid, 2-furaldehyde, nicotinaldehyde, and so forth. In preferred embodiments, the aldehyde may be formaldehyde, cyclopropane carboxaldehyde, or cyclobutane carboxaldehyde. In an exemplary embodiment, the aldehyde may be formaldehyde. The molar ratio of compound 7 to aldehyde may range from about 1:0.5 to about 1:2, or more preferably from about 1:0.8 to about 1:1.2.

In general, the proton donor or proton acceptor will have a pH of less than about 9. Suitable proton donors include, but are not limited to, HOAc, HCO$_2$H, n-PrCO$_2$H, PhCO$_3$H, MeSO$_3$H, poly H$_3$PO$_4$, H$_3$PO$_4$, H$_2$SO$_4$, HCl, HBr, HI, CF$_3$SO$_3$H, p-methyltoluenesulfonic acid, and combinations thereof. Suitable proton acceptors include borate salts (such as, for example, NaBO$_3$), di- and tri-basic phosphate salts (such as, for example, Na$_2$HPO$_4$ and Na$_3$PO$_4$, and the like), bicarbonate salts (such as, for example, NaHCO$_3$, KHCO$_3$, LiHCO$_3$, and the like), carbonate salts (such as, for example, Na$_2$CO$_3$, K$_2$CO$_3$, Li$_2$CO$_3$, and the like), organic bases (such as, for example, pyridine, triethylamine, diisopropylethylamine, N-methylmorpholine, N,N-dimethylaminopyridine), and mixtures thereof. Other suitable proton acceptors/proton donors include N,N-bis-(2-hydroxyethyl)-glycine (BICINE), N-[tris(hydroxymethyl)methyl]glycine (TRICINE), tris(hydroxymethyl)aminomethane (TRIS), 3-(cyclohexylamino)-1-propanesulfonic acid (CAPS), 3-(cyclohexylamino)-2-hydroxy-1-propanesulfonic acid (CAPSO), N-(2-hydrooxyethyl)piperazine-N'-(3-propanesulfonic acid) (EPPS), N-2-hydroxyethylpiperazine-N'-2-ethanesulfonic acid (HEPES), 2-(N-morpholino)ethanesulfonic acid (MES), 3-(N-morpholino)propanesulfonic acid (MOPS), piperazine-N,N'-bis(2-ethanesulfonic acid) (PIPES), 3-{[tris(hydroxymethyl)]amino}-1-propanesulfonic acid (TAPS), and N-tris(hydroxymethyl)methyl-2-amino-ethanesulfonic acid (TES). In a preferred embodiment, the proton donor or proton acceptor may be HCO$_2$H, HOAc, MeSO$_3$H, or triethylamine. The molar ratio of compound 7 to proton donor or proton acceptor may range from 1:0.1 to about 1:5, or more preferably from about 1:0.5 to about 1:2.

The reaction is typically conducted in the presence of a solvent. The solvent may be an aprotic polar solvent, a non-polar solvent, or combinations thereof. Non-limiting examples of suitable solvents include acetone, acetonitrile, benzene, butanone, chloroform, 1,2-dichloroethane, dichloromethane, diethyl ether, diethoxymethane, dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, dimethylacetamide (DMAC), N-methylpyrrolidinone (NMP), dioxane, ethyl acetate, ethyl formate, ethyl methyl ketone, formamide, hexamethylphosphoramide, hexane, n-propyl acetate, isopropyl acetate, methyl acetate, N-methylacetamide, N-methylformamide, methyl t-butyl ether, methyl butyl ketone, methylene chloride, nitrobenzene, nitromethane, propionitrile, sulfolane, tetramethylurea, tetrahydrofuran (THF), toluene, trichloromethane, and combinations thereof. In preferred embodiments, the solvent may be acetone, acetonitrile, butanone, chloroform, 1,2,-dichloroethane, dichloromethane, ethyl acetate, n-propyl acetate, isopropyl acetate, methyl t-butyl ether, methyl butyl ketone, tetrahydrofuran, toluene, or combinations thereof. The weight ratio of solvent to compound 7 may range from about 0.5:1 to about 10:1 (g/g).

The temperature of the reaction may range from about 00° C. to about 120° C., and more preferably from about 10° C. to about 80° C. The reaction is preferably performed under ambient pressure. Typically, the reaction is allowed to proceed for a sufficient period of time until the reaction is complete, as determined by chromatography (e.g., HPLC). In this context, a "completed reaction" generally means that the reaction mixture contains a significantly diminished amount of compound 7 and a significantly increased amount of compound 9 compared to the amounts of each at the beginning of the reaction. The yield of compound 9 may be at least about 80%, at least about 85%, at least about 90%, at least about 95%, or at least about 99.9%.

The optical activity of compound 7 and compound 9 may be either (−) or (+). The configuration of C-14 in compound 7 may be either R or S, and the configuration of C-14 and C-8, respectively, in compound 9 may be RR, RS, SR, or SS.

(b) Reaction Scheme 2: Conversion of Compound 6 to Compound 9

Reaction Scheme 2 comprises a process in which asymmetric compound 6 undergoes a ring closure in the presence of an aldehyde and an asymmetric transition metal complex to form the substituted berbine, compound 9, as depicted below:

Reaction Scheme 2

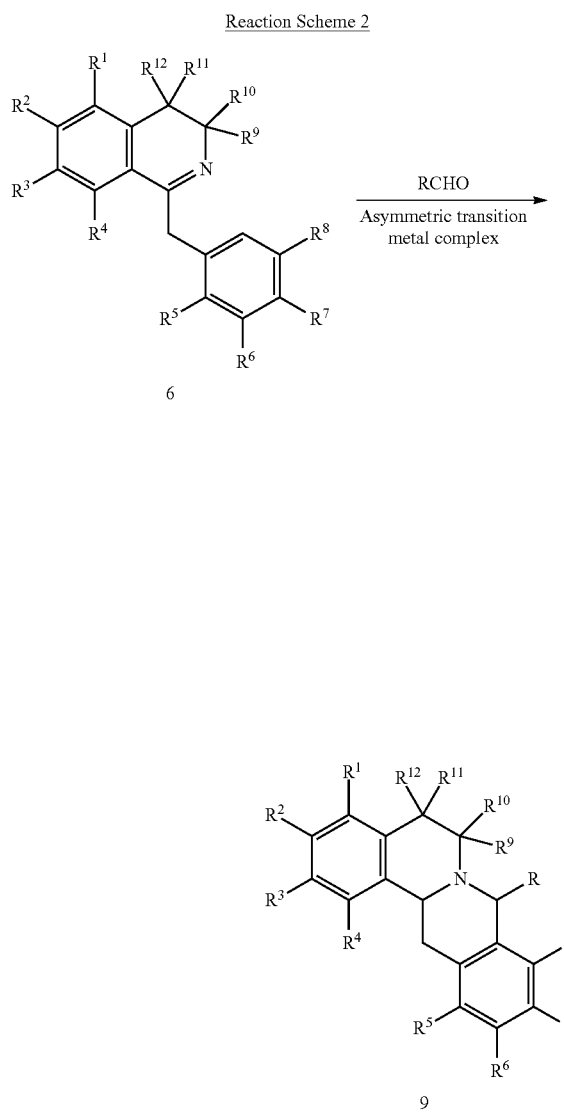

wherein:

R is selected from the group consisting of hydrogen, hydrocarbyl, and substituted hydrocarbyl;

$R^1$, $R^4$, $R^5$, and $R^8$ are independently selected from the group consisting of hydrogen, halogen, $OR^{13}$, $NO_2$, hydrocarbyl, and substituted hydrocarbyl;

$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising {—}O(CH$_2$)$_n$O{—}, and $R^6$ and $R^7$ together with the aromatic carbons to which they are attached may form a ring comprising {—}O(CH$_2$)$_n$O{—};

$R^9$, $R^{10}$, $R^{11}$, and $R^{12}$ are independently selected from the group consisting of hydrogen, hydrocarbyl, and substituted hydrocarbyl;

$R^{13}$ is selected from the group consisting of hydrogen, hydrocarbyl, and substituted hydrocarbyl, preferably an alkyl group with 1 to 8 carbon atoms; and n is an integer from 1 to 3.

In an alternative of this embodiment, R is selected from the group consisting of hydrogen, alkyl, aryl, carboxylic acid, and a heterocyclic ring; and $R^9$, $R^{10}$, $R^{11}$, and $R^{12}$ are each hydrogen. In a preferred alternative of this embodiment, R is hydrogen.

The process of Reaction Scheme 2 comprises contacting compound 6 with an aldehyde in the presence of an asymmetric transition metal complex to form compound 9. Examples of suitable and preferred aldehydes are presented above in section (II)(a). The molar ratio of compound 6 to aldehyde may range from about 1:0.5 to about 1:2, or more preferably from about 1:0.8 to about 1:1.2.

The asymmetric transition metal complex comprises a metal or a metal ion selected from the group consisting of Co, Cr, Ir, Ni, Pd, Pt, Rh, and Ru. Exemplary asymmetric transition metal complexes include dichloro-(p-cymene)-Ru(II) dimer. The molar ratio of compound 6 to asymmetric transition metal complex may range from about 1:0.001 to about 1:1, or more preferably from about 1:0.005 to about 1:0.5.

The reaction is typically conducted in the presence of a solvent. Examples of suitable and preferred solvents are presented above in section (II)(a). The weight ratio of solvent to compound 6 may range from about 0.5:1 to about 10:1 (g/g).

The temperature of the reaction may range from about 00° C. to about 120° C., and more preferably from about 10° C. to about 80° C. The reaction is preferably performed under ambient pressure, and preferably in an inert atmosphere (e.g., nitrogen or argon). Typically, the reaction is allowed to proceed for a sufficient period of time until the reaction is complete, as determined by chromatography (e.g., HPLC).

The yield of compound 9 generally is at least about 80%. In some embodiments, the yield of compound 9 may be about 85%, about 90%, about 95%, or about 99.9%. The optical activity of compound 9 may be either (−) or (+). The configuration of C-14 and C-8, respectively, in compound 9 may be RR, RS, SR, or SS.

(c) Reaction Scheme 3: Two-Step Process for the Conversion of Compound 6 to Compound 9

Reaction Scheme encompasses a two-step process for the conversion of asymmetric compound 6 to the substituted berbine, compound 9, according to the following scheme:

Reaction Scheme 3

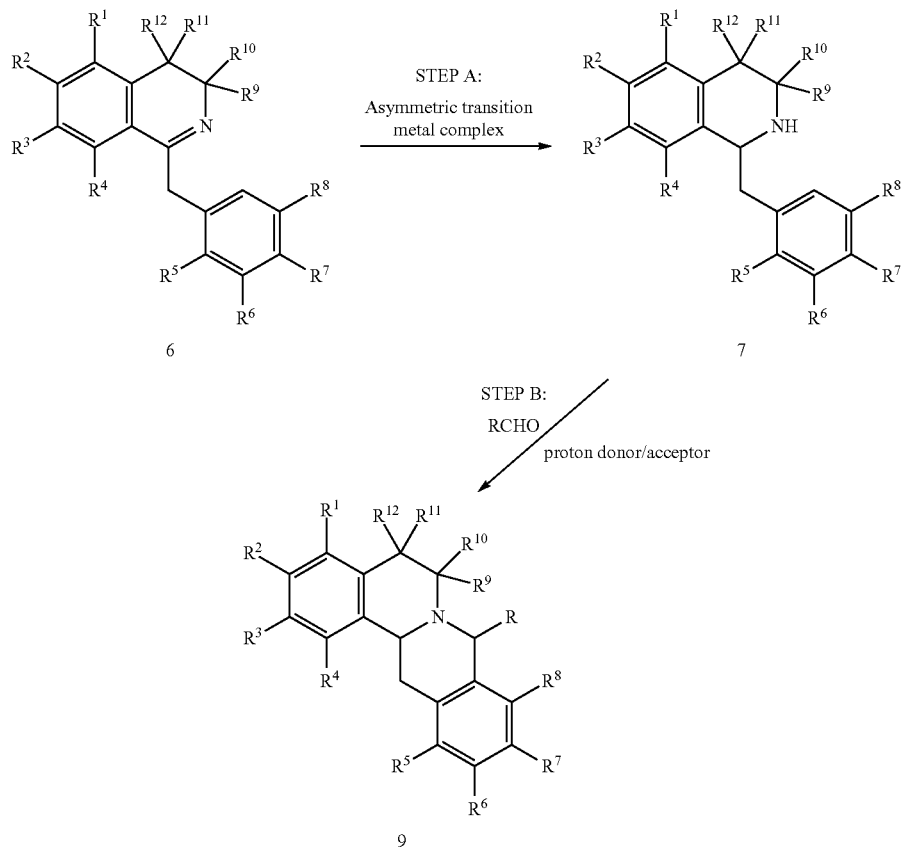

wherein
R is selected from the group consisting of hydrogen, hydrocarbyl, and substituted hydrocarbyl;
$R^1$, $R^4$, $R^5$, and $R^8$ are independently selected from the group consisting of hydrogen, halogen, $OR^{13}$, $NO_2$, hydrocarbyl, and substituted hydrocarbyl;
$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising {—}O$(CH_2)_n$O{—}, and $R^6$ and $R^7$ together with the aromatic carbons to which they are attached may form a ring comprising {—}O$(CH_2)_n$O{—};
$R^9$, $R^{10}$, $R^{11}$, and $R^{12}$ are independently selected from the group consisting of hydrogen, hydrocarbyl, and substituted hydrocarbyl;
$R^{13}$ is selected from the group consisting of hydrogen, hydrocarbyl, and substituted hydrocarbyl, preferably an alkyl group with 1 to 8 carbon atoms; and
n is an integer from 1 to 3.

In an alternative of this embodiment, R is selected from the group consisting of hydrogen, alkyl, aryl, carboxylic acid, and a heterocyclic ring; and $R^9$, $R^{10}$, $R^{11}$, and $R^{12}$ are each hydrogen. In a preferred alternative of this embodiment, R is hydrogen.

In step A of Reaction Scheme 3, compound 6 is contacted with an asymmetric transition metal complex to form compound 7. Examples of suitable and preferred asymmetric transition metal complexes are presented above in section (II)(b). The molar ratio of compound 6 to asymmetric transition metal complex may range from about 1:0.001 to about 1:1, or more preferably from about 1:0.005 to about 1:0.5.

In step B of Reaction Scheme 3, the asymmetric compound 7 undergoes a ring closure to form compound 9. For this, compound 7 is contacted with an aldehyde in the presence of a proton donor or a proton acceptor. Examples of suitable and preferred aldehydes are presented above in section (II)(a). Likewise, examples of suitable and preferred proton donors and proton acceptors are presented in section (II)(a). The molar ratio of compound 7 to aldehyde to proton donor/acceptor may range from about 1:0.5:0.1 to about 1:2:5, or more preferably from about 1:0.8:0.5 to about 1:1.2:2.

Both steps of the process are typically performed in the presence of a solvent. Examples of suitable and preferred solvents are detailed above in section (II)(a). The temperature of both steps of the reaction may range from about 0° C. to about 120° C., and more preferably from about 10° C. to about 80° C. The reaction is preferably performed under ambient pressure, and may be performed in an inert atmosphere (e.g., nitrogen or argon). Typically, the reaction is allowed to proceed for a sufficient period of time until the reaction is complete, as determined by chromatography (e.g., HPLC).

The yield of compound 9 generally is at least about 80%. In some embodiments, the yield of compound 9 may be about 85%, about 90%, about 95%, or about 99.9%. The optical activity of compound 7 and compound 9 may be either (−) or (+). The configuration of C-14 in compound 7 may be R or S, and the configuration of C-14 and C-8, respectively, in compound 9 may be RR, RS, SR, or SS.

(d) Reaction Scheme 4: Conversion of Compound 6c to Compound 9x.

Reaction Scheme 4 provides a three-step process for the conversion of asymmetric compound 6c to the substituted berbine, compound 9x, as depicted below:

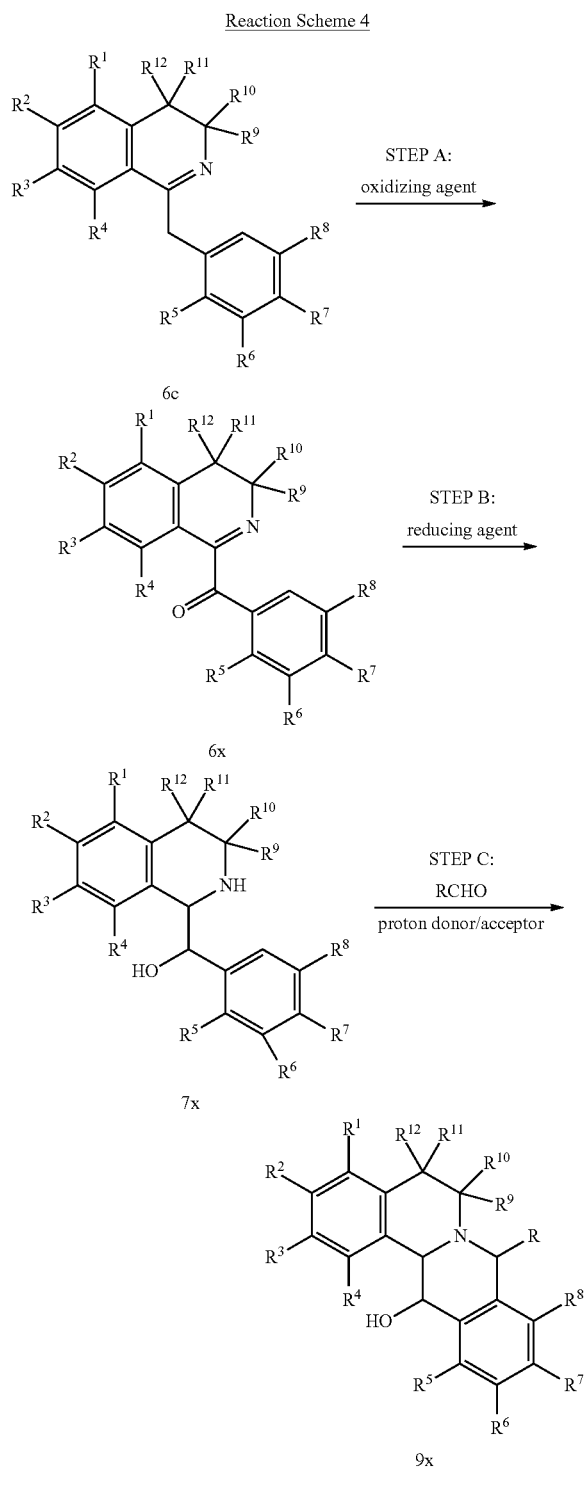

wherein:

R is selected from the group consisting of hydrogen, hydrocarbyl, and substituted hydrocarbyl;

$R^1$, $R^4$, $R^5$, and $R^8$ are independently selected from the group consisting of hydrogen, halogen, $OR^{13}$, $NO_2$, hydrocarbyl, and substituted hydrocarbyl;

$R^2$, $R^3$, $R^6$, and $R^7$ are independently selected from the group consisting of hydrogen, halogen, $OR^{13}$, hydrocarbyl, and substituted hydrocarbyl, provided that $R^2$ and $R^3$ together with the aromatic carbons to which they are attached may form a ring comprising {—}O(CH$_2$)$_n$O{—}, and $R^6$ and $R^7$ together with the aromatic carbons to which they are attached may form a ring comprising {—}O(CH$_2$)$_n$O{—};

$R^9$, $R^{10}$, $R^{11}$, and $R^{12}$ are independently selected from the group consisting of hydrogen, hydrocarbyl, and substituted hydrocarbyl;

$R^{13}$ is selected from the group consisting of hydrogen, hydrocarbyl, and substituted hydrocarbyl, preferably an alkyl group with 1 to 8 carbon atoms; and n is an integer from 1 to 3.

In an alternative of this embodiment, R is selected from the group consisting of hydrogen, alkyl, aryl, carboxylic acid, and a heterocyclic ring; and $R^9$, $R^{10}$, $R^{11}$, and $R^{12}$ are each hydrogen. In a preferred alternative of this embodiment, R is hydrogen.

(i) Step A: Conversion of Compound 6c to Compound 6x

In step A of Reaction Scheme 4, compound 6c is oxidized on C-13 to form compound 6x. The process comprises contacting compound 6c with an oxidizing agent. Examples of oxidizing agents that may be used include, but are not limited to, dichromates (e.g., ammonium dichromate, potassium dichromate, sodium dichromate, and the like); bromates (e.g., barium bromate, magnesium bromate, potassium bromate, sodium bromate, and the like); chlorates (e.g., ammonium chlorate, barium chlorate, calcium chlorate, potassium chlorate, sodium chlorate, and the like); chlorites (e.g., copper chlorite, lead chlorite, potassium chlorite, sodium chlorite, and the like); chloroisocyanuric acids (e.g., trichloroisocyanuric acid, and the like); chromates (e.g., potassium chromate, and the like); chromium oxides (e.g., chromic anhydride (chromium trioxide)); dichromates (e.g., sodium dichromate, potassium dichromate, and the like); hydrogen peroxide; hypobromites (e.g., sodium hypobromite, and the like); hypochlorites (e.g., calcium hypochlorite, potassium hypochlorite, sodium hypochlorite, and the like); hypoiodites (e.g., sodium hypoiodite, potassium hypoiodite, and the like); inorganic peroxides (e.g., barium peroxide, calcium peroxide, cesium peroxide, lithium peroxide, magnesium peroxide, potassium peroxide, rubidium peroxide, sodium peroxide, strontium peroxide, and the like); iodates (e.g., calcium iodate, potassium iodate, sodium iodate, zinc iodate, and the like); iodine oxides (e.g., diiodine pentaoxide, and the like); lead oxides (e.g., lead dioxde, and the like); manganese dioxide; nitrates (e.g., ammonium nitrate, ammonium cerium nitrate, barium nitrate, potassium nitrate, silver nitrate, sodium nitrate, and the like); nitric acid; nitrites (e.g., potassium nitrite, sodium nitrite, and the like); perchlorates (e.g., ammonium perchlorate, potassium perchlorate, sodium perchlorate, and the like); periodates (e.g., potassium periodate, sodium periodate, and the like); periodic acids (e.g., metaperiodic acid, and the like); permanganates (e.g., ammonium permanganate, magnesium permanganate, potassium permanganate, sodium permanganate, and the like); peroxoborates (e.g., ammonium peroxoborate, and the like); perchloric acid; peroxodisulfates (e.g., ammonium peroxodisulfates, potassium peroxydisulfate, and the like); peroxyacids (e.g., peroxyacetic acid, peroxybenzoic acid, peroxyformic acid, trifluoroperacetic acid, and the like); organic peroxides (e.g., benzoyl peroxide, and the like); tetroxides (e.g., osmium tetroxide, ruthenium tetroxide, and the like); and oxygen. As the oxygen source, air may also be used. The molar ratio of compound 6c to oxidizing agent may range from about 1:0.5 to about 1:5, or more preferably from about 1:0.8 to about 1:2.

Step A of the process is typically conducted in the presence of a solvent. Examples of suitable and preferred solvents are presented above in section (II)(a). The weight ratio of solvent to compound 6c may range from about 0.5:1 to about 10:1 (g/g). Step A of Reaction Scheme 4 is generally conducted at ambient pressure and at a temperature that ranges from about 00° C. to about 120° C., and more preferably from about 10° C. to about 80° C.

(ii) Step B: Conversion of Compound 6x to Compound 7x

In step B of Reaction Scheme 4, compound 6x undergoes catalytic reduction to form compound 7x. In this step of the process, compound 6x is contacted with a reducing agent such that the oxygen function on C-13 is reduced to a hydroxyl group. Representative reducing agents for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. In a preferred embodiment, the reducing agent may be sodium cyanoborohydride. The molar ratio of compound 6x to reducing agent may range from about 1:0.5 to about 1:3, or more preferably from about 1:0.8 to about 1:2.

Step B is generally conducted in the presence of a solvent. Examples of suitable and preferred solvents are presented above in section (II)(a). The weight ratio of solvent to compound 6c may range from about 0.5:1 to about 10:1 (g/g). The reaction may be conducted at a temperature that ranges from about 00° C. to about 120° C., or more preferably from about 10° C. to about 80° C. Step B generally is conducted at ambient pressure, and preferably in an inert atmosphere.

(iii) Step C: Conversion of Compound 7x to Compound 9x

In step C of Reaction Scheme 4, compound 7x undergoes a ring closure to form compound 9x. For this, compound 7x is contacted with an aldehyde in the presence of a proton donor or a proton acceptor. Examples of suitable and preferred aldehydes and are presented in section (II)(a). Similarly, examples of suitable and preferred proton donors, and proton acceptors are also presented in section (II)(a). The molar ratio of compound 7x to aldehyde to proton donor/ acceptor may range from about 1:0.5:0.1 to about 1:2:5, or more preferably from about 1:0.8:0.5 to about 1:1.2:2. Suitable solvents and weight ratios of solvent to compound 7x are as detailed in section (II)(a). The temperature of step C may range from about 00° C. to about 120° C., or more preferably from about 10° C. to about 80° C.; and reaction is generally conducted at ambient pressure.

The yield of compound 9x generally is at least about 80%. In some embodiments, the yield of compound 9x may be about 85%, about 90%, about 95%, or about 99.9%.

The optical activity of compound 7x, and compound 9x may be either (−) or (+). The configuration of C-13 and C-14, respectively, in compound 7x may be RR, RS, SR, or SS, and the configuration of C-13, C-14, and C-8, respectively, in compound 9x may be RRR, RRS, RSR, RSS, SRR, SRS, SSR, or SSS.

(e) Reaction Scheme 5: Conversion of Compound 8 to Compound 10.

Reaction Scheme 5 encompasses a process for the conversion of compound 8 to compound 10, as depicted below:

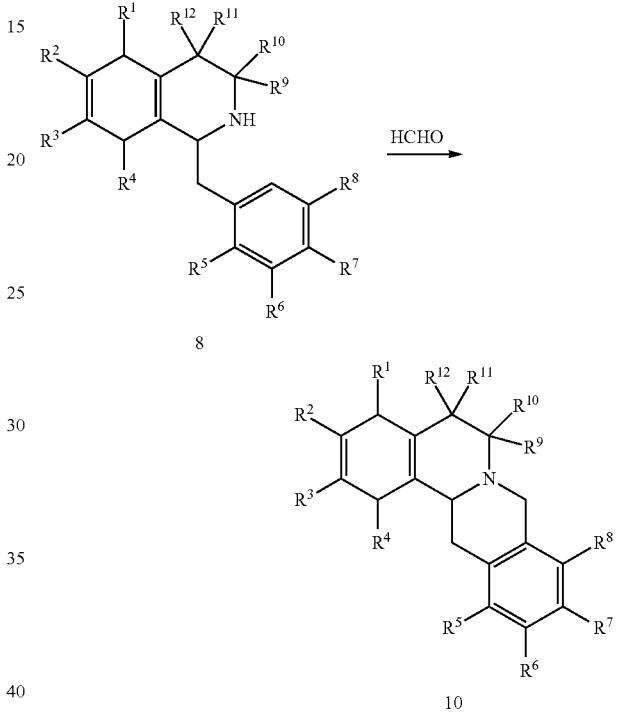

wherein:
$R^1$, $R^4$, $R^5$, and $R^8$ are independently selected from the groups consisting of hydrogen, halogen, $OR^{13}$, $NO_2$, hydrocarbyl, and substituted hydrocarbyl;
$R^2$, $R^3$, $R^6$, and $R^7$ are independently selected from the groups consisting of hydrogen, halogen, $OR^{13}$, hydrocarbyl, and substituted hydrocarbyl; provided that $R^2$ and $R^3$ together with the aromatic carbons to which they are attached may form a ring comprising {—}O $(CH_2)_nO${—}, and $R^6$ and $R^7$ together with the aromatic carbons to which they are attached may form a ring comprising {—}O$(CH_2)_nO${—};
$R^9$, $R^{10}$, $R^{11}$, and $R^{12}$ are independently selected from the group consisting of hydrogen, hydrocarbyl, and substituted hydrocarbyl;
$R^{13}$ is selected from the group consisting of hydrogen, hydrocarbyl, and substituted hydrocarbyl, preferably an alkyl group with 1 to 8 carbon atoms; and
n is an integer from 1 to 3.

In an alternative of this embodiment, $R^9$, $R^{10}$, $R^{11}$, and $R^{12}$ are each hydrogen.

The process of Reaction Scheme 5 comprises contacting compound 8 with formaldehyde to form compound 10. The molar ratio of compound 8 to formaldehyde may range from about 1:0.8 to about 1:1.2, or more preferably from about 1:0.9 to about 1:1.1. Typically, the process is conducted in the presence of a solvent. Examples of suitable and preferred solvents are presented above in section (II)(a). The weight ratio of solvent to compound 8 may range from about 0.5:1 to about 10:1 (g/g). Generally, the process is conducted at ambient pressure and at a temperature that ranges from about 00° C. to about 120° C., or more preferably from about 10° C. to about 80° C. The yield of compound 10 typically may range form about 80% to about 99.9%.

The optical activity of compound 8 and compound 10 may be (−) or (+). The configuration of C-14 in compound 8 may be R or S, and the configuration of C-14 in compound 10 may be R or S.

Definitions

To facilitate understanding of the invention, several terms are defined below.

The term "acyl," as used herein alone or as part of another group, denotes the moiety formed by removal of the hydroxy group from the group COOH of an organic carboxylic acid, e.g., RC(O), wherein R is $R^1$, $R^1O-$, $R^1R^2N-$, or $R^1S-$, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The compounds described herein may have asymmetric centers. Compounds containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

As various changes could be made in the above compounds and processes without departing from the scope of the invention, it is intended that all matter contained in the above description and in the examples given below, shall be interpreted as illustrative and not in a limiting sense.

EXAMPLES

The following examples illustrate various embodiments of the invention.

Example 1: Synthesis of Compound 8 from Compound 7

Compound 8 was prepared from compound 7 according to the following reaction scheme:

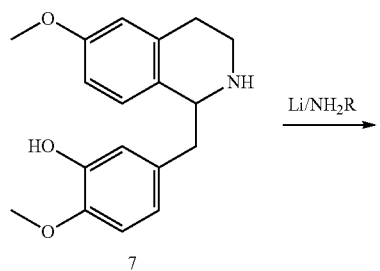

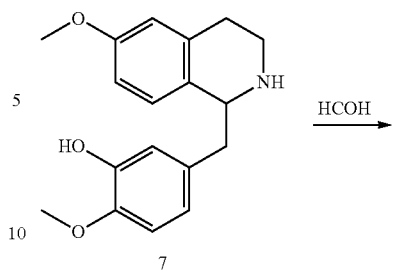

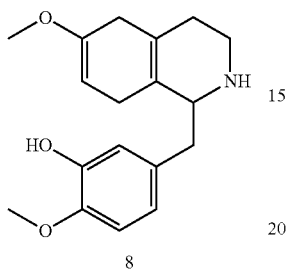

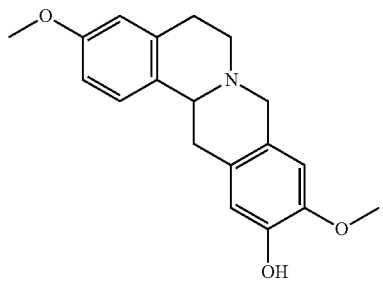

To a reactor, isopropyl alcohol (2.0 mL/g of compound 7), tetrahydrofuran (4.0 mL/g of compound 7) and compound 7 (pre-dried until the limit of detection was <0.2%) were added. The suspension was cooled to −55° with stirring over a dry-ice bath. To the reactor, liquid ammonia (10 mL/g of compound 7) was condensed at −55° C. The reaction mixture was cooled at −55° C. and was flushed with nitrogen for 15 min. NaOBu-t (0.35 g/g of compound 7) was added and stirred for another 15 min. Lithium (cut, 0.070 g/g of compound 7) was added in three portions to the mixture (each portion=1/3×0.070 g/g of compound 7) and the temperature of the reaction mixture was maintained at about −45° C. to −55° C. using a dry-ice bath and by controlling the addition rate. The reaction mixture was stirred for 50 min or until all of the lithium was added. If the blue color of the reaction mixture lasted for more than 30 min the reaction was complete; otherwise, more lithium was added until the blue color persisted. Methanol (1.0 g/g of compound 7) was added after the reaction was deemed complete. The reaction mixture was warmed to about −28° C. to +20° C. to evaporate off most of the ammonia and stirred for another hour after the temperature reached +20° C. Degassed water (10 mL/g of compound 7) (prepared by bubbling with nitrogen for 20 min) was added under nitrogen to the above mixture. The suspension was stirred for 30 min to form a solution (pH=12.4). A solution of acetic acid/water (HOAc 0.95 ml/g of compound 7, and $H_2O$ 1.90 mL/g of compound 7) was added to form a suspension (pH=7.8). The pH of the suspension was adjusted to about pH 8.8-9.2 with 28% ammonium hydroxide (about 0.25 mL/g of compound 7). The suspension was stirred for 1 h and filtered. The reactor was repeatedly rinsed with water (3.0 mL/g of compound 7), which was then used to wash the solid filtrate. The solid was then washed with water (3.0 mL/g of compound 7). The solid was dried under flowing air for 4 h and then dried in vacuum (20 inches) at 60° C. for 20 h to the produce (compound 8) as an off-white solid with a yield around 90%.

Example 2: Synthesis of Compound 9 from Compound 7

Compound 9 was prepared from compound 7 according to the following:

Compound 7 (3 g) was refluxed in acetronitrile/chloroform (15 mL/30 mL). A solution of formaldehyde (1 M) in $H_2O$/acetonitrile (1:9, 11 mL) was added. The mixture was heated to reflux for another 3 h to form a suspension. About 20 mL of the solvent was removed by distillation. The resulting suspension was cooled to room temperature and filtered. The solid was washed with isopropyl alcohol (2×5 mL) and dried under vacuum at 50° F. for 4 h to give 2.3 g of compound 9 as a solid.

Example 3: Synthesis of Compound 9 from Compound 6

Compound 9 was prepared from compound 6 according to the following scheme:

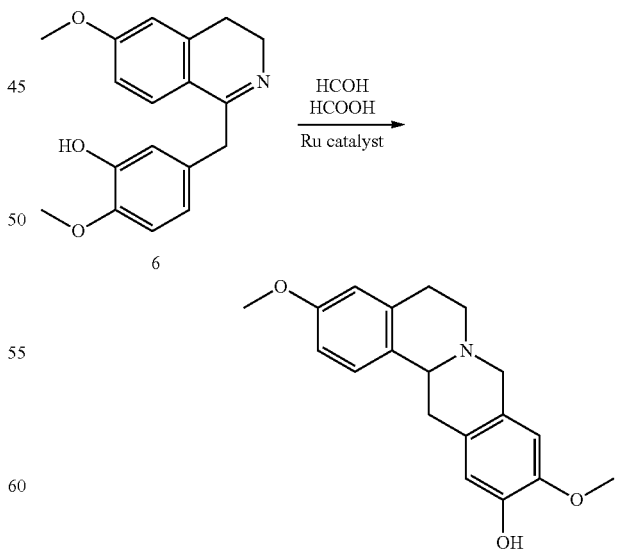

To a reactor equipped with mechanical stirrer, triethylamine (NEt₃) (1.06 g per gram of compound 6) and acetonitrile (6 mL per gram of compound 6) were added. Formic acid (HCO$_2$H) (1.2 g per gram of compound 6) was added in four portions. The exothermic reaction was maintained at a temperature of less than 80° C. during the addition. Upon cooling to room temperature, a solution of 5HCO$_2$H/2NEt$_3$ in acetonitrile was formed. Compound 6 was added to the solution to form a suspension. After flushing with nitrogen for 15 min, dichloro (p-cymene)-Ru(II) dimer (0.01 g per gram of compound 6) was added. The suspension was again flushed with nitrogen for 15 min and stirred at room temperature for 10 h. A solution of formaldehyde (1 M) in H$_2$O/acetonitrile (1:9, 3.5 mL per gram of compound 6) was added. The reaction mixture was heated over 100° C. for 2 h to form compound 9. The product was isolated as a solid by pouring the solution into an ice-cold ammonium hydroxide (NH$_4$OH) solution (20 mL per gram of compound 6).

Example 4: Synthesis of C-8 Cyclopropyl Derivative of Compound 9

The cyclopropyl derivative of compound 9 was prepared from the (R) isomer of compound 7 according to the following reaction scheme:

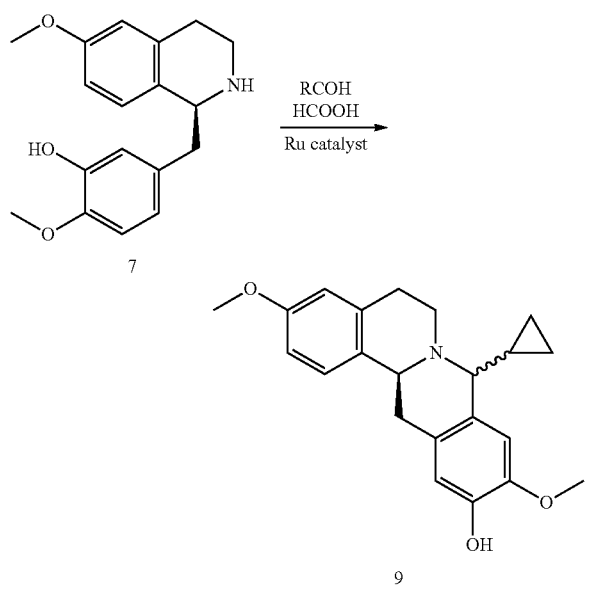

A stirred solution of compound 7 (0.5 g), methanol (3 mL), cyclopropane carboxaldehyde (0.175 mL), triethylamine (1.86 mL), and formic acid (0.77 mL) was heated to reflux and maintained at reflux for 1 hour. The reaction mixture was then cooled to 40° C., and dichloro (p-cymene)-Ru(II) dimer (0.01 g) was added. The resulting mixture was stirred at 40° C. overnight. After cooling to room temperature, the reaction was diluted with water (3 mL) and the pH was adjusted to 9.0 with NH$_4$OH. The precipitate was collected by vacuum filtration and dried to give the product as a light yellow solid. The structure of the product was confirmed by LC-NMR and LC-MS.

Example 5: Synthesis of C-8 Cyclobutyl Derivative of Compound 9

The cyclobutyl derivative of compound 9 was prepared from the (R) isomer of compound 7 according to the following reaction scheme:

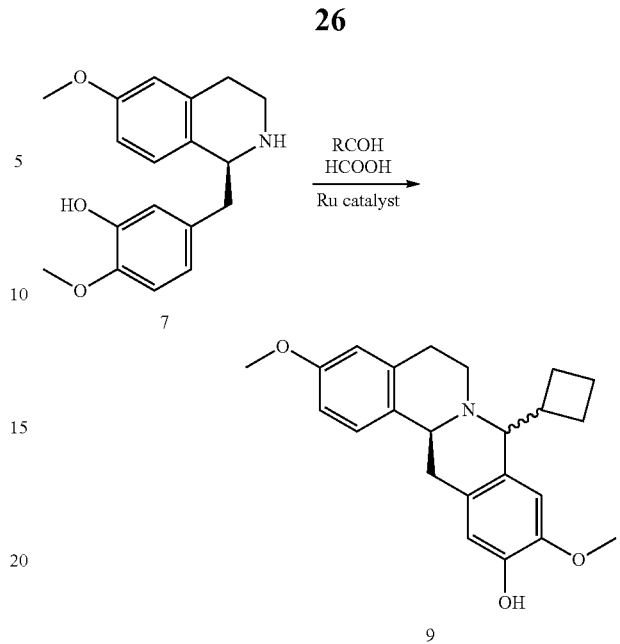

A stirred solution of compound 7 (0.5 g), methanol (3 mL), cyclobutane carboxaldehyde (0.175 mL), triethylamine (1.86 mL), and formic acid (0.77 mL) was heated at reflux for 1 hour. The reaction mixture was then cooled to 40° C., and dichloro (p-cymene)-Ru(II) dimer (0.01 g) was added. The resulting mixture was stirred at 40° C. overnight. After cooling to room temperature, the reaction was diluted with water (3 mL) and the pH adjusted to 9.0 with NH$_4$OH. The precipitate was collected by vacuum filtration and dried to give the product as a light yellow solid. The structure of the product was confirmed by LC-NMR and LC-MS.

Example 6: Alternate Synthesis of C-8 Cyclobutyl Derivative of Compound 9

The cyclobutyl derivative of compound 9 was prepared from the (R) isomer of compound 7 according to the following reaction:

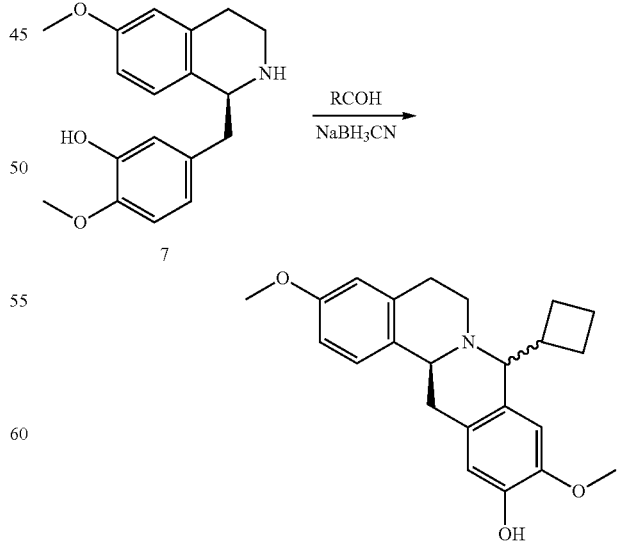

A solution of compound 7 (0.5 g) and cyclobutane carboxaldehyde (0.212 mL) in acetonitrile (3 mL) was heated at 40° C. for 1 hour. Sodium cyanoborohydride (0.16 g) was then added, and the resulting mixture was stirred at 40° C. overnight. After cooling to room temperature, the reaction mixture was diluted with water (3 mL) and the pH adjusted to 9.0 with NH$_4$OH. The precipitate was collected by vacuum filtration and dried to give the product as a light yellow solid. The structure of the product was confirmed by LC-NMR and LC-MS.

What is claimed is:

1. A process for preparing compound 9, the process comprising forming a reaction mixture in which compound 6 is contacted with dichloro-(p-cymene)-Ru(II) dimer and formic acid-triethylamine to form compound 7, and adding RCHO to the reaction mixture to form compound 9 according to the following reaction scheme:

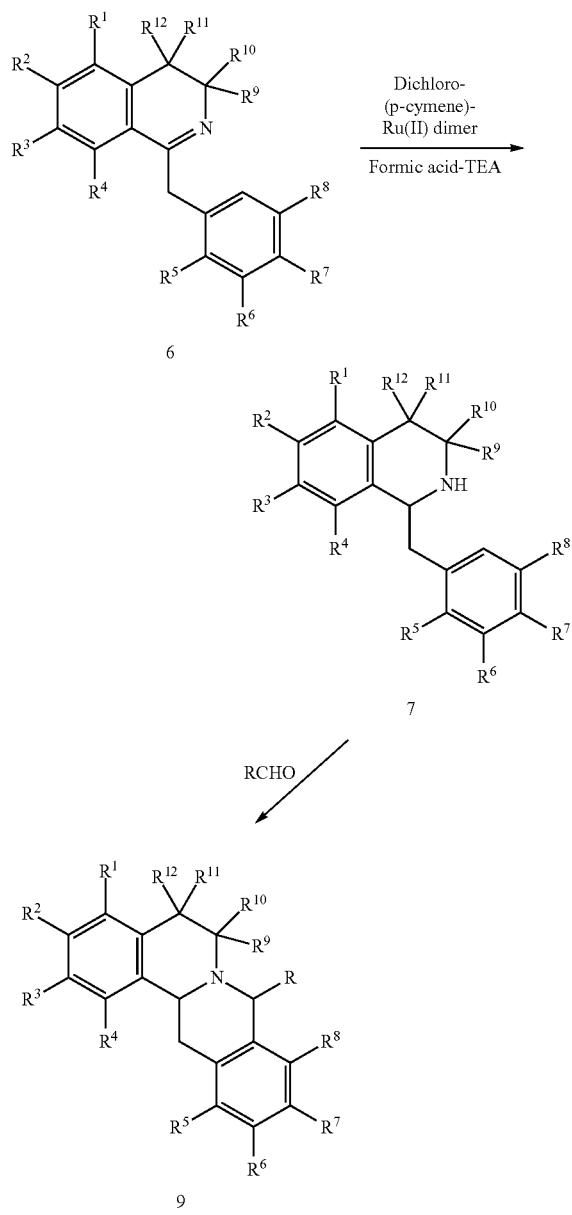

wherein:

R is selected from the group consisting of hydrocarbyl and substituted hydrocarbyl;

$R^1$, $R^2$, $R^3$, and $R^4$ are independently selected from the group consisting of hydrogen, halogen, $OR^{13}$, hydrocarbyl, substituted hydrocarbyl, and together $R^2$ and $R^3$ form $\{-\}O(CH_2)_nO\{-\}$;

$R^5$, $R^6$, $R^7$, and $R^8$ are independently selected from the group consisting of hydrogen, halogen, $OR^{13}$, hydrocarbyl, substituted hydrocarbyl, and together $R^6$ and $R^7$ form $\{-\}O(CH_2)_nO\{-\}$;

$R^9$, $R^{10}$, $R^{11}$, and $R^{12}$ are independently selected from the group consisting of hydrogen, hydrocarbyl, and substituted hydrocarbyl;

$R^{13}$ is selected from the group consisting of hydrogen, hydrocarbyl, and substituted hydrocarbyl; and n is an integer from 1 to 3.

2. The process of claim 1, wherein R is selected from the group consisting of alkyl, substituted alkyl, aryl, and substituted aryl, and $R^{13}$ is alkyl.

3. The process of claim 1, wherein each of $R^9$, $R^{10}$, $R^{11}$, and $R^{12}$ is hydrogen.

4. The process of claim 1, wherein $R^1$, $R^2$, $R^3$, and $R^4$ are independently selected from the group consisting of hydrogen, $OR^{13}$, and together $R^2$ and $R^3$ form $\{-\}O(CH_2)_nO\{-\}$; and $R^5$, $R^6$, $R^7$, and $R^8$ are independently selected from the group consisting of hydrogen, $OR^{13}$, and together $R^6$ and $R^7$ form $\{-\}O(CH_2)_nO\{-\}$; wherein $R^{13}$ is hydrogen or an alkyl having 1 to 8 carbon atoms, and n is 1 to 3.

5. The process of claim 1, wherein compound 7 and RCHO are present at a molar ratio of about 1:0.5 to about 1:2.

6. The process of claim 1, wherein the reaction is conducted in the presence of a solvent selected from the group consisting of acetone, acetonitrile, butanone, chloroform, 1,2,-dichloroethane, dichloromethane, ethyl acetate, n-propyl acetate, isopropyl acetate, methanol, methyl t-butyl ether, methyl butyl ketone, tetrahydrofuran, toluene, and combinations thereof.

7. The process of claim 1, wherein the reaction is conducted is conducted at a temperature ranging from about 00° C. to about 120° C.

8. The process of claim 1, wherein compound 9 has a yield of at least about 80%.

9. The process of claim 1, wherein R is alkyl; $R^1$, $R^2$, $R^3$, and $R^4$ are independently selected from the group consisting of hydrogen, $OR^{13}$, and together $R^2$ and $R^3$ form $\{-\}O(CH_2)O\{-\}$; $R^5$, $R^6$, $R^7$, and $R^8$ are independently selected from the group consisting of hydrogen, $OR^{13}$, and together $R^6$ and $R^7$ form $\{-\}O(CH_2)O\{-\}$; and each of $R^9$, $R^{10}$, $R^{11}$, and $R^{12}$ is hydrogen, wherein $R^{13}$ is hydrogen or methyl.

10. The process of claim 9, wherein the reaction is conducted in the presence of a solvent selected from the group consisting of acetonitrile, chloroform, methanol, and combinations thereof.

11. The process of claim 10 wherein the reaction is conducted is conducted at a temperature ranging from about 10° C. to about 80° C.

12. The process of claim 11, wherein compound 9 has a yield of about 80% to about 99.9%.

* * * * *